United States Patent
Hedin et al.

[11] Patent Number: 5,900,234
[45] Date of Patent: May 4, 1999

[54] SEX PHEROMONE COMPOSITION FOR PECAN WEEVIL

[75] Inventors: Paul A. Hedin, Starkville, Miss.; Justin K. Collins, Gaymon; Raymond D. Eikenbary, Stillwater, both of Okla.

[73] Assignee: The United States of America as represented by the Secretary of Agriculture, Washington, D.C.

[21] Appl. No.: 08/965,839

[22] Filed: Nov. 7, 1997

[51] Int. Cl.$^6$ ..................................... A01N 25/00
[52] U.S. Cl. .................. 424/84; 424/405; 43/107
[58] Field of Search .................. 424/84, 405; 43/107

[56] References Cited

U.S. PATENT DOCUMENTS 4,456,587  6/1984  Keith ........................................ 424/78

FOREIGN PATENT DOCUMENTS

00294175A1  12/1988  European Pat. Off. .

OTHER PUBLICATIONS

Tumlinson et al, Identification and synthesis of four compounds comprising the boll weevil sex attractant, J. Org. Chem., 36: 2616–2621, 1971.

*Primary Examiner*—Thurman K. Page
*Assistant Examiner*—Lakshmi Channavajjala
*Attorney, Agent, or Firm*—M. Howard Silverstein; John D. Fado; Joseph A. Lipovsky

[57] ABSTRACT

A sex pheromone composition effective in the attraction of female pecan weevils has been found, and comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3-dimethylcyclohexane-$\Delta^{1,\alpha}$-acetaldehyde] in the approximate ratio of 7:16:3:3. The compositions have use as mating disruptants and as attractants for the purpose of population control or monitoring.

4 Claims, No Drawings

SEX PHEROMONE COMPOSITION FOR PECAN WEEVIL

BACKGROUND OF THE INVENTION

1. Field of the Invention

This invention relates to a pheromonally based composition and methods for its use in the control of the pecan weevil, Curculio caryae (Horn).

2. Description of the Prior Art

The pecan weevil, *Curculio caryae* (Horn) is a serious economic pest of pecans (*Caryae illinoensis* Koch), attacking maturing fruit in late summer and causing damage thereto through the making of feeding and oviposition punctures. The larvae, upon completing development in the nut, leave through a small hole in the shell and burrow into the soil. The weevils remain there for a period of 2–3 years before emerging as adults to commence another cycle.

Van Cleave and Harp in an article entitled "The Pecan Weevil: Present Status and Future Prospectives" (*Proc. 64th Ann. Conv. Southeast Pecan Growers Assoc.* pp. 99–111, 1971), reported that field-caged female pecan weevils attracted more weevils of both sexes than did caged male weevils. Polles et al. in an article entitled "Attraction of the Pecan Weevil to its Natural Pheromone and Grandlure" (*Pecan South* 4:26–28, 1977), reported on field studies in which wing-type traps, each baited with 6 live females and pecan nutlets for food, captured 85 pecan weevils (73% males). The same number of traps, baited with males captured 56 weevils (66% males), and blank traps captured 55 weevils (65% males). Polles et al., also baited traps with one or more of the components of the pheromone of the boll weevil *Anthonomus grandis* grandis Boheman (Tumlinson et al., "Identification and Synthesis of the Four Compounds Comprising the Boll Weevil Sex Attractant" *J. Org. Chem.* 36:2616–2621, 1971), on the premise that related insects may biosynthesize and respond to related compounds. A total of 23 pecan weevils (87% male), were captured with the 4-component mixture, grandlure. With (+)-cis-2-isopropenyl-1-methylcyclobutaneethanol (Component I alone), the captures totaled 7 (86% males); with (Z)-3,3-dimethyl-$\Delta^{1,\beta}$-cyclohexaneethanol (II), there were 15 (100% males); and with (Z) and (E)-3,3-dimethyl-$\Delta^{1,}$-cyclohexaneacetaldehyde (III and IV), there were 10 (90% males). However, the blank captured about as many as did individual components: 10 weevils (70% males). Therefore, none of these tests were sufficiently comprehensive to permit statistical evaluations and in no instance was further work reported.

Mody et al., in an article entitled "Pecan Weevil Sex Attractant: Bioassay and Chemical Studies" (*J. Insect. Physiol.* 19:2063–2071, 1973), bioassayed fractions obtained from volatile oils of each sex of pecan weevils in field tests. Primarily males were trapped with female fractions, and primarily females were trapped with male factions. GLC-MS was used to identify a number of volatile components from the male and female oils, but on the basis of their structures, none appeared capable of accounting for the attractancy of either sex.

Hedin et al., "Sex Pheromones of the Male and Female Pecan Weevil, Curculio caryae: Behavioral and Chemical Studies" (*Environ. Entomol.* 8:521–523, 1979), showed that male and female pecan weevils were attractive to their opposite sex using a newly developed laboratory bioassay. Extracts of males attracted females and vice versa. (Z)-3,3-dimethyl-$\Delta^{1,\beta}$-cyclohexaneethanol was identified as present in a weevil extract and shown to possess some attractiveness to both sexes in preliminary field bioassays, used either as adsorbents or catalysts.

While various methodologies and pheremonal compositions exist for the control of other insect species, there remains a need for the creation of such tools for use with the pecan weevil.

SUMMARY OF THE INVENTION

We have now discovered that female pecan weevils may be effectively attracted by a four component pheromone system comprising a mixture of substantially pure components, said components comprising I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3-dimethylcyclohexane-$\Delta^{1,\alpha}$-acetaldehyde] in the approximate ratio of 7:16:3:3.

Therefore, it is an object of this invention to provide an attractant for female pecan weevils which will allow for effective detection and monitoring of the adult population.

Another object is to provide an attractant which may be used for mating disruption and/or capture of pecan weevils.

Other objects and advantages of the invention will become readily apparent from the ensuing description.

DETAILED DESCRIPTION OF THE INVENTION

The composition of the present invention comprises a sex pheromone composition effective in the attraction of female pecan weevils comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV)[(E)-3,3-dimethylcyclohexane-$\Delta^{1,\alpha}$-acetaldehyde] in the approximate ratio of 7:16:3:3 (wt/wt). Structural formulas for these compounds are as follows:

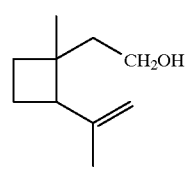

(I)

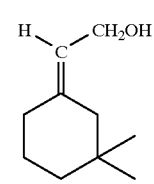

(II)

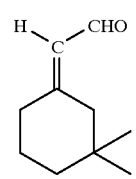

(III)

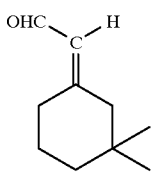

(IV)

The amounts of the components, expressed on a weight ratio basis, is comparable to that naturally occurring in the presence of other constituents including: 1-methyl-cyclopentanol, 3-hexanol, phenol, N-decane and N-nonanal, in the male pecan weevil. Due to the occurrence of natural variability within the species as to the exact proportional ratios of these components, all proportional ratios wherein one or more components vary by ±10% are considered to be within the scope of the present invention. The term approximate, as used in the application in this regard, is defined to be of equal scope with this ±10% variation. Each individual component is commercially available (MTM Chemicals, Columbus, Ohio) in substantially pure form (e.g. 99% pure), or may be produced or isolated in substantially pure form using art-known techniques.

In order to apply an effective amount of the composition for the purpose of eliciting a behavioral response in adult female pecan weevils, the composition may be incorporated as part of a pheromone dispenser. As used herein, the term dispenser is meant to include a substrate such as a membrane, flake, hollow fiber, microcapsule or the like. All these substrates are at present commercially available and have previously been employed with sex pheromones in the combating of insect pests.

EXAMPLE 1

In accordance with the procedures outlined in the publication "Identification of Male Pecan Weevil Pheromone" (Hedin et al.; *Journal of Chemical Ecology*, Vol. 23, No. 4, pp.965–977; 1997), hereby incorporated by reference, insect extracts were obtained by the following procedures. After capture, individual weevils were placed in vials and transported to the laboratory, sexed, and then transferred to 200-ml glass feeding chambers with immature pecans for 5 days. Individual pairs of males and females were then placed in 28-ml glass jars with Teflon lids. In two tests, male/female washings were collected by rinsing the chamber after removal of the pair with methylene chloride (ca. ml; Test A) or alternatively hexane(Test B), after the males had mounted and assumed the mating posture. The washings were then transferred to an amber glass bottle, combined with the other replicates, and stored at −20° C.

In four other tests, pairs were placed in mating chambers and observed until excitation occurred, but males were not allowed to mount or assume a mating posture. The individuals were separated and males (tests C and D) and females (tests E and F) were washed with 1 ml of methylene chloride. Replicate washings were combined and stored at −20° C. The summary of collections was as follows: A-68 M/F, 5 days old, in methylene chloride; B-68 M/F, 5 days old, in hexane; C-68 males, 5 days old, in methylene chloride; D-68 males, 5 days old, in methylene chloride (replicate); E-68 females, 5 days old, in methylene chloride; and F-68 females, 5 days old, in methylene chloride (replicate).

Extractions, Fractionations, and Gas Chromatography Mass Spectral Analysis of Insects. A 1×30-cm column equipped with a bulb and frit was filled with a slurry of 6 g of Baker silica gel (60–200 mesh, 3405-05) in hexane (Optima, Fischer Scientific). Previous to application of the extract to the column, the insects that had been stored at −20° C. under hexane or hexane-methylene chloride were ground in a Polytron homogenizer. The entire contents were applied to the column, which was then washed first with 125 ml hexane and then with 125 ml of methylene chloride. Each fraction was concentrated to 1 ml or less for GLC-MS. The fractions were monitored using silica gel TLC plates that were chromatographed with 50% methylene chloride in hexane and visualized in an iodine chamber. It was determined that the hexane eluate consisted mostly of hydrocarbons, and a separate column chromatographic test demonstrated that compounds I, II, III, and IV (as shown above) were not eluted with hexane but with methylene chloride.

All GLC-MS analyses (except for one) were performed with a DB-1 column (J&W Scientific, Folsom, Calif.; 30 m×0.32 mm ID×0.25-µm layer thickness), injection temperature 280° C., transfer line 300° C., 5 min hold; split ratio 15:1.

A chiral column, Beta-Dex 120 (Supelco, Inc., Bellefonte, Pa. 30 m×0.25 mm ID×0.25-µm thickness), operated at a column temperature of 150° C., injection temperature 180° C., detector 250° C., FID, split ratio 80:1, was employed to separate the (+) and (−) isomers of component I. The columns were interfaced with a Hewlett-Packard HP-5989 quadruple mass spectrometer operated in the EI mode. Spectral interpretations were supported by the NIST/EPA/MSDC Mass Spectral Database 1A PC Version 3.0 (Lias and Stein, 1990), and the HP 59944C MS Chem System Version 8.05 (1992).

GLC-MS analyses on the six collections of male, female and mixed body washings and extracts gave 28 significant maxima, of which structural assignments were made for 19. Unambiguous mass spectral data for the presence of pheromone components I, II, III, and IV were obtained from male collections C and D, while male/female collections A and B contained only the more prevalent components I and II. Female collections E and F did not contain any of these constituents. Mass spectra of the four small maxima between 6.5 and 7.2 min were those of compounds I, II, III, and IV. From the total ion count, the content from 68 males was determined to be 0.29 µg/insect of I+II+III+IV. The distribution was approximately 0.07 µg I, 0.16 µg II, 0.03 µg III, and 0.03 µg IV.

EXAMPLE 2

Formulations based on the chemical ratios found by the analyses in Example 1 were dispersed in laminates prepared by Hercon Environmental Corporation, Emigsville, Pa., so that 2.5-cm-square sections contained 10 mg of the prescribed four-component mixtures. Hercon Luretape is a laminated, three-layered plastic dispenser; a reservoir layer contains the active ingredients that are sandwiched between two outer permeable layers of polyvinyl chloride film. The inner layer is also a polyvinyl chloride film. Laminates of the commercial boll weevil formulation were procured from Hercon.

Laboratory tests were done to determine the relative attractiveness of the synthetic formulations of: (1) the pecan weevil pheromone, (2) the commercial boll weevil pheromone, (3) a synthetic formulation based on the ratio of components in boll weevil frass, and (4) live pecan weevil males to both sexes of the pecan weevil. The bioassays were carried out in a choice olfactometer in which the airflow was calibrated at 25 ml/min. The candidate pheromone lure or live males were also placed in one arm of the olfactometer with no lure in the other arm. Virgin, unfed males or females were introduced into the olfactometer between 0900 and 1400 hr, which had been determined to be the hours of maximum mating activity of the pecan weevil. Responses of the insects were recorded after 1 hr. For each candidate pheromone tested, 100 replications were employed, except for the boll weevil frass formulation where 50 replications were employed. The data were analyzed using the chi-square procedure on all possible pairwise combinations. Significant differences were observed between all combinations at P<0.05 except one. The data on percent attractiveness are summarized in Table 1.

TABLE 1

Olfactometer Tests of Relative Attractiveness of Three Synthetic Pheromone Formulations and Virgin Female and Male Pecan Weevils.

| Sex responding | Pecan weevil pheromone 7:16:3:3 | Boll weevil pheromone 3:4:1.5:1.5 | Boll weevil frass 6:6:1.5:1.5 | Live males | Live females |
|---|---|---|---|---|---|
| Female (%) | 80 | 60 | 28 | 43 | |
| Male (%) | 14 | 4 | 2 | 0 | 0 |

Preliminary field experiments showed that synthetic formulations based on the male pecan weevil pheromone ratio were significantly more effective than synthetic formulations based on the commercial boll weevil ratio or unbaited traps (P>0.05). A t test grouped the control and the boll weevil pheromone together with a mean of 0.55 and 0.88 females per trap, respectively. Traps employing the pecan weevil pheromone captured a mean of 5.00 females per trap with a LSD of 1.67.

It is understood that the foregoing detailed description is given merely by way of illustration and that modifications and variations may be made therein without departing from the spirit and scope of the invention.

We claim:

1. A method of attracting female pecan weevils to a trap comprising the employment as a lure on said trap of an effective amount of a pheromonal composition comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3-dimethylcyclohexane-$\Delta^{1,\alpha}$-acetaldehyde] in the approximate ratio of 7:16:3:3 (wt/wt).

2. A method of disrupting the mating activities of the pecan weevil comprising dispersing a synthetic pheromone composition into an area infested with said moths effective to permeate the air throughout said area with false pheromone signals, said composition comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3 dimethylcyclohexane-$\Delta^{1,\alpha}$-acetaldehyde] in the approximate ratio of 7:16:3:3 (wt/wt).

3. A sex pheromone composition for female pecan weevils comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3-dimethylcyclohexane-$\Delta^{1,\alpha}$-acetaldehyde] in the approximate ratio of 7:16:3:3 (wt/wt).

4. A pheromone dispenser for pecan weevils, said dispenser impregnated with a pheromone composition comprising a mixture of substantially pure components, said components comprising: I) a racemic mixture of the cis and trans isomers of 2-isopropenyl-1-methylcyclobutaneethanol, II) [(Z)-3,3-dimethylcyclohexane-$\Delta^{1,\beta}$-ethanol], III) [(Z)-3,3-dimethylcyclohexane-$\Delta^{1,\alpha}$-acetaldehyde], and IV) [(E)-3,3-dimethylcyclohexane-$\Delta^{1,\alpha}$-acetaldehyde] in the approximate ratio of 7:16:3:3 (wt/wt).

* * * * *